United States Patent
Glowa et al.

[11] Patent Number: 6,086,542
[45] Date of Patent: Jul. 11, 2000

[54] PRESSURE SENSING INPUT/OUTPUT SCOPE SHEATH

[75] Inventors: Michael P. Glowa, St. Petersburg; James Everett Crawford, Tampa, both of Fla.

[73] Assignee: Linvatec Corporation, Largo, Calif.

[21] Appl. No.: 09/104,680

[22] Filed: Jun. 25, 1998

Related U.S. Application Data

[60] Provisional application No. 60/051,454, Jul. 1, 1997.

[51] Int. Cl.[7] .................................................. A61B 5/00
[52] U.S. Cl. .............................. 600/561; 604/27; 604/43; 600/140
[58] Field of Search ...................... 600/561, 104, 600/117, 130, 139, 140, 156; 604/27, 31, 43, 65, 66, 118

[56] References Cited

U.S. PATENT DOCUMENTS

| | | | |
|---|---|---|---|
| 5,037,386 | 8/1991 | Marcus et al. | 604/43 |
| 5,108,364 | 4/1992 | Takezawa et al. | 604/43 |
| 5,211,631 | 5/1993 | Sheaff | 604/113 |
| 5,718,678 | 2/1998 | Flemming, III | 604/43 |
| 5,800,383 | 9/1998 | Chandler et al. | 604/65 |
| 5,810,770 | 9/1998 | Chin et al. | 604/65 |
| 5,814,016 | 9/1998 | Valley et al. | 604/96 |
| 5,840,060 | 11/1998 | Beiser et al. | 604/66 |
| 5,908,407 | 6/1999 | Frazee et al. | 604/101 |

*Primary Examiner*—Eric F. Winakur
*Assistant Examiner*—Charles Marmor, II
*Attorney, Agent, or Firm*—Gene Warzecha

[57] ABSTRACT

A single instrument is provided for simultaneously enabling fluid inflow, fluid outflow and pressure sensing during endoscopic surgical procedures. The instrument comprises three concentric tubular members, each of which has a distal end and a proximal end and each of which has a port connected to its proximal end for providing access to the interior of the associated tubular member. Each of the tubular members is coaxially aligned with the others and the central most tubular member is adapted to enable an elongated endoscopic instrument to be inserted axially therethrough. The invention also resides in the method of sensing pressure within a body cavity by utilizing such an instrument which enables a user to perform fluid inflow, fluid outflow and pressure sensing simultaneously.

9 Claims, 4 Drawing Sheets

PRESSURE SENSING INPUT/OUTPUT SCOPE SHEATH

This application claims the benefit of U.S. Provisional Application No. 60/051,454 filed on Jul. 1, 1997.

BACKGROUND OF THE INVENTION

1. Field of the Invention

The invention relates to devices used in endoscopic surgical procedures. In particular, the invention relates to pressure sensing devices used in arthroscopic surgical procedures. Still more particularly, the invention relates to pressure sensing scope sheaths used in arthroscopic surgical procedures in order to simultaneously provide instrument or scope access to the arthroscopic work site while also providing a means for communicating pressure information from the work site, a means for fluid inflow and a means for fluid outflow.

2. Description of the Prior Art

In endoscopic surgical procedures and, in particular, in arthroscopic procedures, there is often a need to know the pressure at the surgical work site. For example, in some arthroscopic surgical procedures the joint being operated on is subjected to irrigating fluid pressure in order to distend the joint to provide an adequate work space and in order to keep the joint free of debris while enhancing visibility during the procedure. An outflow channel is provided to maintain fluid movement through the work site. The fluid may be pressurized by a pump which forces the fluid into the work site, or it may simply be pressurized by gravity. While a certain degree of pressure is necessary, an excessive amount of pressure may cause extravasation into surrounding tissue or otherwise injure the patient. Consequently, pressure sensing devices are used during many arthroscopic surgical procedures in order to control the fluid pressure being supplied to the work site.

Pressure sensing devices may be provided in a variety of configurations depending upon the surgeon's preference and the particular surgical procedure. Also, different surgical techniques require a different number of portals to gain access to the surgical site. Common techniques for operative arthroscopy require two or three portals at the work site while diagnostic arthroscopy may be performed with two portals. For example, in arthroscopic surgery of the knee using a three-portal technique, one pressure sensing cannula assembly may be provided through one portal in the knee while a second portal is used for an arthroscope and a third portal is used for an operating instrument such as a powered rotary shaver system. The pressure sensing cannula has two channels: one for inflow to communicate the pressurized fluid to the knee capsule and another to communicate pressure to a pressure sensor.

Alternatively, a dedicated pressure sensing cannula in one portal may be provided to provide pressure sensing information to a sensor while another cannula in another portal may be used to provide instrument access and a third cannula in a third portal may be used to provide access for an arthroscope (or the scope may be used without a cannula).

Another prior art system utilizes a dual stopcock pressure sensing scope sheath designed to work with a particular pump system made by the same manufacturer. This sheath has a central, axial lumen for scope access and a surrounding annular channel joined to separate inflow and outflow stopcocks at its proximal end. The stopcocks share this single annular channel which is used alternatingly for both inflow and outflow. The annular space between the scope and the inside of the central cannula provides pressure information to a port at the proximal end of the sheath. While this system may be used with only a two portal technique, the alternating nature of the system operation makes many surgeons use it in a three portal technique, with the third portal used for pressure sensing.

There is a preference to minimize the number of portals required in endoscopic and arthroscopic procedures. Consequently, it is an object of this invention to provide a surgical instrument which can provide access to an endoscopic surgical work site while minimizing the number of portals required by utilizing a single portal for pressure sensing information in addition to fluid inflow and fluid outflow.

It is also an object of this invention to provide a single instrument having a plurality of channels capable of performing fluid inflow, fluid outflow and pressure sensing simultaneously.

It is an additional object of this invention to provide a method for sensing pressure using such an instrument.

It is yet another object of this invention to provide a cannula or sheath which can receive a scope therethrough while simultaneously enabling a user to perform fluid inflow, fluid outflow and pressure sensing.

SUMMARY OF THE INVENTION

These and other objects of this invention are achieved by the preferred embodiment disclosed herein which is a pressure sensing input/output surgical instrument for providing a fluid inflow channel, a fluid outflow channel and a pressure sensing channel. The instrument comprises an elongated inner tubular member having a lumen, a distal end, a proximal end and a fluid port at the proximal end in communication with the lumen thereof, the lumen adapted to receive an elongated instrument therein and provide a fluid outflow channel. This inner tubular member may receive an arthroscope, endoscope or the like. The instrument also comprises an elongated intermediate tubular member having a lumen, a distal end, a proximal end and a fluid port at the proximal end in communication with the lumen thereof, the intermediate member coaxially situated about the inner member and defining an annular pressure sensing channel between the inner member and the intermediate member. The instrument also comprises an elongated outer tubular member having a lumen, a distal end, a proximal end and a fluid port in communication with the lumen thereof, the outer member coaxially situated about the intermediate member and defining an annular fluid inflow channel between the outer member and the intermediate member.

The invention also resides in a method of sensing the pressure of fluid within a body cavity during a surgical procedure while enabling fluid inflow and outflow. The method comprises the steps of providing a first tubular member having a first channel, providing a second tubular member aligned with the first tubular member and having a second channel, and providing a third tubular member aligned with the second tubular member and having a third channel. All of the tubular members are aligned to enable the method to be performed through a single portal. The third tubular member is adapted to receive therein an elongated member and to simultaneously provide a fluid outflow path from the distal end of the third tubular member to its proximal end. The method further comprises the steps of communicating fluid to the body cavity through the first channel and communicating pressure information from the distal end of the second member to the proximal end thereof through the second channel.

DESCRIPTION OF THE PREFERRED EMBODIMENT

Figure 1:
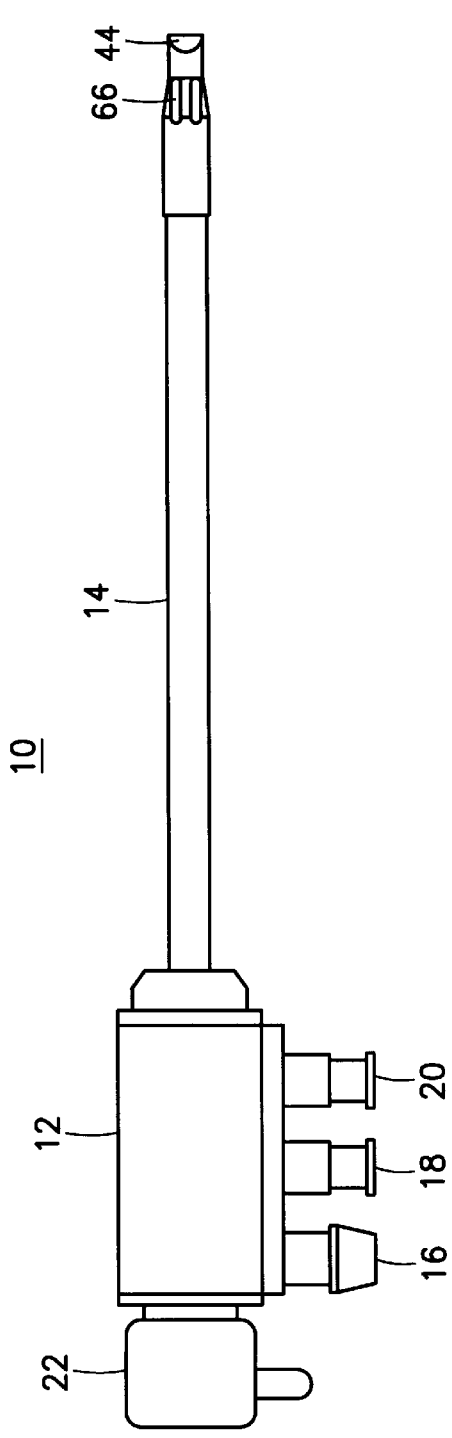
FIG. 1 is a plan view of a pressure sensing input/output scope sheath constructed in accordance with the principles of this invention.

A pressure sensing input/output scope sheath 10 constructed in accordance with the principles of this invention is shown in FIG. 1. Sheath 10 comprises a body 12 to which is attached a distally extending insertion section 14, a plurality of connecting ports 16, 18 and 20 and a locking means 22.

Figure 2:
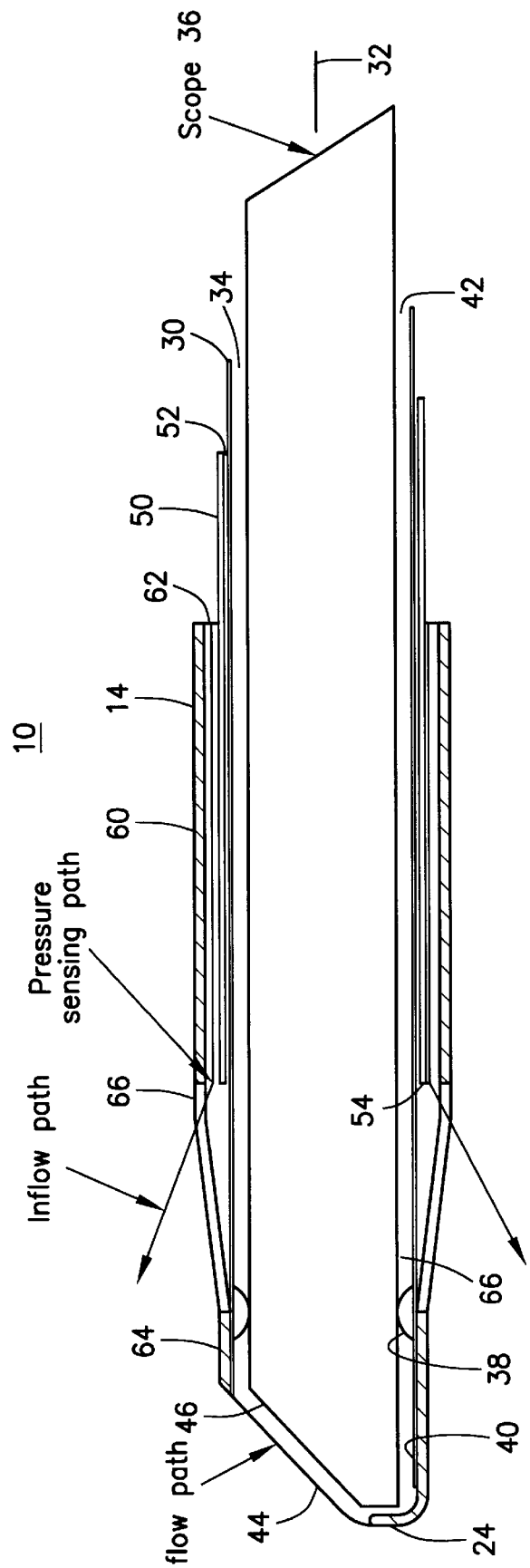
FIG. 2 is a cross-sectional view of the distal tip of the instrument of FIG. 1.
Figure 3:
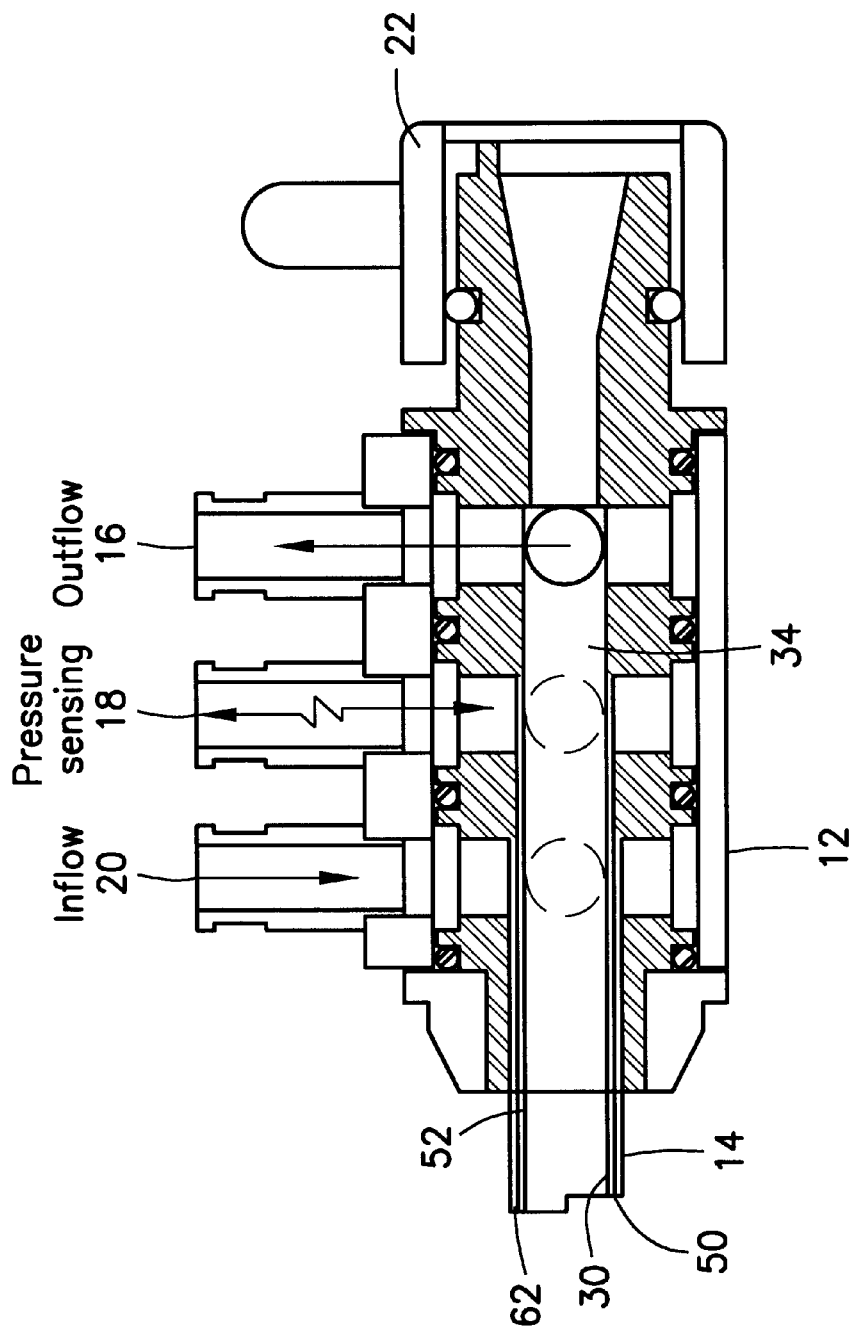
FIG. 3 is a cross-sectional view of the proximal end of the instrument shown in FIG. 1.

In the preferred embodiment insertion section 14, best seen in FIG. 2, comprises three concentric tubular members each having a proximal end terminating within body 12 and a distal end terminating at the distal tip 24 of the sheath. Thus, in cross-section the insertion section would appear as a plurality of concentric circles. As will be understood below, various other cross-sectional profiles could be configured. Inner tubular member 30 has an axis 32 and an interior lumen 34 which provides access for an elongated member such as a surgical instrument in the form of, for example, an arthroscope 36. A plurality of annularly arranged dimples 38 is provided adjacent the distal end 40 of the inner tube in order to axially align the scope within the lumen of the inner member. When the scope is inserted into the inner member, an annular chamber 42 is created so that fluid may be drawn from the work site through annular channel 42 and out the outflow port 16 in body 12.

While the instrument shown received within central lumen 34 is an arthroscope 36, it will be understood that other surgical instruments could also be inserted into sheath 10 if desired. It is noted, however, that sheath 10 is particularly suited for operation with a scope 36 in that distal end 24 is angled to receive the distal tip of the scope and has an aperture 44 through which the tip of the scope may view the surgical work site. Additionally, the intersection of annular channel 42 with aperture 44 creates an annular inflow port around the distal tip 46 of the scope in order to create sufficient fluid flow around this transparent face of the scope in order to continually clear the area of any debris or obstructions to visibility.

An intermediate elongated tubular member 50 is situated coaxially about the inner tubular member 30 and produces an annular space 52 between it and the outer surface of the inner member, which annular space 52 is communicated to the pressure sensing port 18 on body 12. Intermediate member 50 has a distal end 54 which is spaced a predetermined distance from the distal tip of the sheath 10.

An outer concentric tubular member 60 is provided outwardly of the intermediate member 50 and produces an annular channel 62 between it and the outer surface of the intermediate member 50, which annular channel 62 is communicated to the inflow port 20 on body 12. The distal end of the outer tubular member 60 is joined at 64 to the distal tip of the inner tubular member 30 and is provided with a plurality of annularly spaced, generally elongated fenestrations 66 in order to permit fluid flowing distally through annular channel 62 to flow evenly into the surgical work site.

Figure 4:
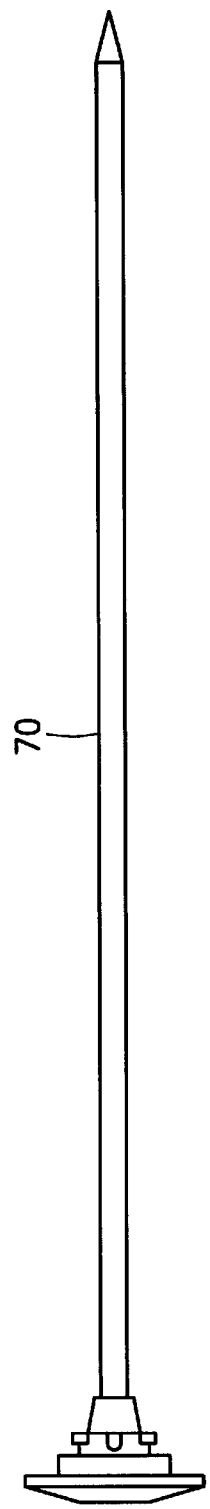
FIG. 4 is a side elevational view of an obturator suitable for use with the instrument shown in FIG. 1.

Locking member 22 is provided with a conventional locking system such as a bayonet lock (not shown) in order to secure sheath 10 to an arthroscopic instrument such as scope 36 or obturator 70, shown in FIG. 4.

In operation, sheath 10 provides a plurality of fluid channels which may be used for inflow, outflow and pressure sensing functions through a single portal. The various channels within sheath 10 are designed to optimize fluid flow while minimizing back pressure or impedance. In the preferred embodiment, annular channel 62 is used for inflow and has a cross-sectional area on the order of 0.0071 square inches. Annular channel 52 is used for pressure sensing and has a cross-sectional area on the order of 0.0086 square inches. Annular channel 42 is used as an outflow channel and its size is dependent upon the size of the scope 36. In one preferred embodiment where the diameter of the scope is 0.159 inches, the annular channel 52 has a cross-sectional area of 0.0062 square inches. The outside diameters of inner member 30, intermediate member 50 and outer member 60 are 0.1848 inches, 0.2182 inches, and 0.250 inches, respectively, and the corresponding inside diameters of these members are 0.178 inches, 0.2122 inches and 0.238 inches, respectively. The relative size relationships between the cross-sectional areas of annular channels 42, 52 and 62 were designed to operate with the APEX fluid pump system manufactured by the assignee hereof although it will be understood by those skilled in the art that similar pressure sensing input/output scope sheaths could be adapted for use with other fluid pump systems.

Figure 5:
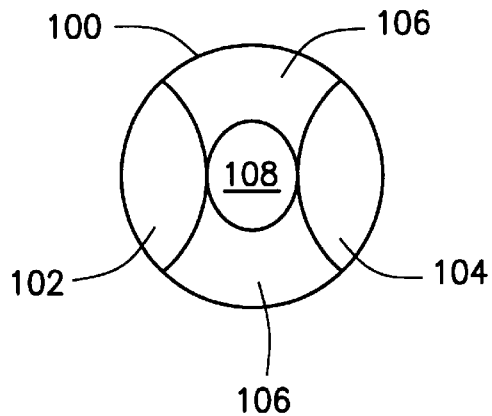
FIG. 5 is a cross-sectional diagrammatic view of an alternative embodiment of a pressure sensing input/output scope sheath.
Figure 6:
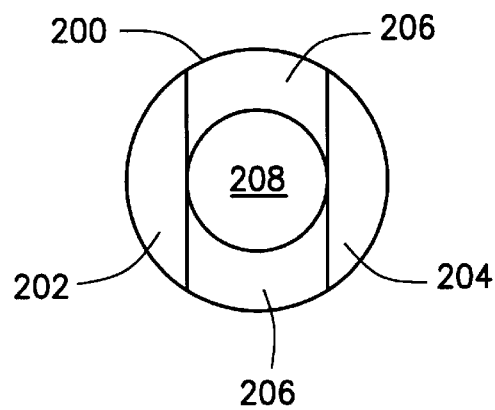
FIG. 6 is a cross-section of a diagrammatic embodiment of an alternative form of a pressure sensing input/output scope sheath.
Figure 7:
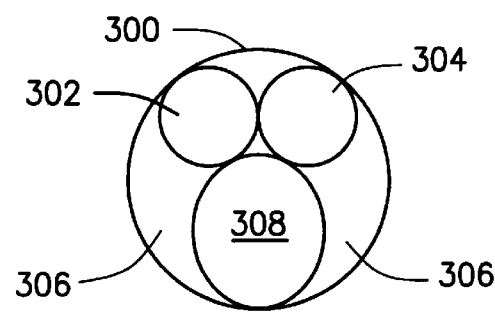
FIG. 7 is a cross-section of a diagrammatic embodiment of an alternative form of a pressure sensing input/output scope sheath.

While the preferred embodiment will be understood to appear as a plurality of concentric circles having annular channels therebetween, it will be understood by those skilled in the art that the various areas represented by annular channels 42, 52 and 62 could be in effect formed by other than concentric circles. For example, one could devise an outer circular tube having compartmentalized channels of various cross-sections extending longitudinally along the tube. As seen in FIGS. 5, 6 and 7, a pressure sensing input/output scope sheath 100 could be produced having a pressure sensing channel 102, an inflow (or outflow) channel 104, an outflow (or inflow) channel 106 and adapted to receive a scope 108. Alternatively, a pressure sensing input/output scope sheath 200 could be produced with a pressure sensing channel 202, an inflow (or outflow) channel 204, and an outflow (or inflow) channel 206 and adapted to receive a scope 208. Yet another alternative could be produced in the form of pressure sensing input/output scope sheath 300 containing a circular pressure sensing channel 302, an outflow channel 304 and an inflow channel 306 and adapted to receive a scope 308. It will be understood that even the outer circular member of all of the embodiments disclosed herein could be formed in other than circular cross-sections such as elliptical, polygonal, etc.

Another aspect of the invention is the method of sensing pressure within an endoscopic work site by using an elongated channel which is inserted through a portal which also provides access to fluid inflow and outflow channels. The steps of this method are achievable by use of the various apparatus embodiments described above by connecting the various ports to appropriate fluid sources, sensors and receptacles and operating same as usual.

It will be understood that numerous variations and modifications may be made to the invention disclosed herein without departing from the spirit and scope thereof.

What is claimed is:

1. A pressure sensing input/output surgical cannula for receiving an elongated instrument and for providing a fluid inflow channel, a fluid outflow channel and a pressure sensing channel comprising:

an elongated inner tubular member having a first lumen, a distal end, a proximal end and a fluid port at said proximal end in communication with said first lumen, said first lumen being open at said distal and proximal ends and sized to receive said elongated instrument therein and provide an annular fluid outflow channel between said instrument and the wall of said first lumen;

an elongated intermediate tubular member having a second lumen, an open annular distal end, a proximal end and a fluid port at said proximal end in communication with said second lumen, said intermediate tubular member coaxially situated about said inner tubular member and defining an annular pressure sensing channel between said inner tubular member and said intermediate tubular member; and an elongated outer tubular member having a third lumen, a distal end, a proximal end and a fluid port in communication with said third lumen, said outer tubular member coaxially situated about said intermediate tubular member and defining an annular fluid inflow channel between said outer tubular member and said intermediate tubular member, said outer tubular member having a conical surface tapered at said distal end toward said inner tubular member, said conical surface provided with a plurality of circumferentially spaced, axially elongated fenestrations.

2. A pressure sensing input/output surgical cannula according to claim 1 further comprising a plurality of projections extending radially inwardly into said first lumen of said inner tubular member for axially aligning said elongated instrument inserted through said first lumen of said inner tubular member.

3. A pressure sensing input/output surgical cannula according to claim 1 wherein said distal end of said outer tubular member is situated a predetermined distance proximally from the distal end of said inner tubular member.

4. A pressure sensing input/output surgical cannula for providing a fluid inflow channel, a fluid outflow channel and a pressure sensing channel comprising:

an elongated first tubular member having a first lumen, a distal end, a proximal end and a fluid port at said proximal end in communication with said first lumen, said first lumen sized to receive an elongated instrument therein and provide an annular fluid outflow channel between said instrument and the wall of said first lumen;

an elongated second tubular member having a second lumen, an open annular distal end, a proximal end and a fluid port at said proximal end in communication with said second lumen, said second tubular member aligned with said first tubular member and defining a pressure sensing channel; and an elongated third tubular member having a third lumen, a distal end, a proximal end and a fluid port in communication with said third lumen, said third tubular member aligned with said first and second tubular members and defining a fluid inflow channel.

5. A method of providing instrument access to an endoscopic work site while enabling fluid inflow, fluid outflow and the sensing of fluid pressure at the work site during a surgical procedure comprising the steps of:

providing a first tubular member having a first channel;

providing a second tubular member aligned with said first tubular member and having a second channel;

providing a third tubular member aligned with said second tubular member and having a third channel, said third tubular member being adapted to receive therein an elongated instrument and to simultaneously provide a fluid outflow path from a distal end of said third tubular member to a proximal end thereof;

inserting an elongated instrument through a lumen of said third tubular member;

communicating fluid to said endoscopic work site through said first channel; and communicating pressure information from a distal end of said second tubular member to a proximal end thereof through said second channel.

6. A method according to claim 5 further comprising the step of:

joining said first, second and third tubular members together in axial alignment.

7. A method according to claim 5 wherein said first, second and third tubular members are coaxially aligned and further comprising the step of:

providing a plurality of fenestrations at a distal end of said first tubular member, said fenestrations extending from said first tubular member to said third tubular member.

8. A method according to claim 5 wherein the first, second and third members are concentric and said first and second channels are, therefore, annular.

9. A method according to claim 7 further comprising the step of:

terminating said pressure sensing second tubular member at a distal point adjacent a proximal end of said fenestrations.

\* \* \* \* \*